United States Patent
Kaercher et al.

(10) Patent No.: US 9,445,792 B2
(45) Date of Patent: Sep. 20, 2016

(54) MEDICAL INSTRUMENT

(71) Applicant: Karl Storz GmbH & Co. KG, Tuttlingen (DE)

(72) Inventors: Daniel Kaercher, Radolfzell (DE); Robin Merz, Furtwangen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 66 days.

(21) Appl. No.: 14/163,769

(22) Filed: Jan. 24, 2014

(65) Prior Publication Data

US 2014/0214011 A1    Jul. 31, 2014

(30) Foreign Application Priority Data

Jan. 25, 2013    (DE) .......................... 10 2013 100 759

(51) Int. Cl.
*A61B 17/00* (2006.01)
*A61B 17/29* (2006.01)

(52) U.S. Cl.
CPC ......... *A61B 17/00234* (2013.01); *A61B 17/29* (2013.01); *A61B 17/2909* (2013.01); *A61B 2017/0046* (2013.01); *A61B 2017/291* (2013.01); *A61B 2017/2904* (2013.01); *A61B 2017/2929* (2013.01); *A61B 2017/2946* (2013.01); *Y10T 74/00* (2015.01)

(58) Field of Classification Search
CPC ............... A61B 17/00234; A61B 2017/2902; A61B 5/4205
USPC .................................................. 464/160–161
See application file for complete search history.

(56) References Cited

U.S. PATENT DOCUMENTS 745,722 A * 12/1903 Freeman .................. A61C 1/12
                                                   279/77
4,471,781 A * 9/1984 Di Giovanni ...... A61B 17/0491
                                                   606/145
5,176,702 A    1/1993 Bales et al.
(Continued)

FOREIGN PATENT DOCUMENTS

DE    102009051515 A1    5/2011
DE    102010024136 A1    12/2011
(Continued)

OTHER PUBLICATIONS

"Spring-load," Merriam-Webster.com, 2013, http://www.merriam-webster.com, Jan. 22, 2016.*

Primary Examiner — Lynsey Crandall
Assistant Examiner — Amanda Steinberg
(74) Attorney, Agent, or Firm — Whitmyer IP Group LLC (57) ABSTRACT

A medical instrument having a shaft, at the proximal end of which a handle is arranged, wherein the shaft is rotatable about its longitudinal axis and can be secured in various positions of rotation relative to the handle via a licking mechanism. In order for a medical instrument with a shaft rotatable about its longitudinal axis to be designed in such a way that, while being easy to handle, it permits a large number of secure and positionally precise rotations of the shaft with respect to the handle, the licking mechanism is designed as a latching mechanism which has a perforated disk with recesses and latching elements, wherein the latching elements and/or the perforated disk are spring-loaded relative to each other, and at least one of the latching elements engages in a corresponding recess of the perforated disk in order to fix the shaft.

15 Claims, 9 Drawing Sheets

(56) References Cited

U.S. PATENT DOCUMENTS

| | | | | |
|---|---|---|---|---|
| 5,376,078 A * | 12/1994 | Dinger, III | A61B 17/32002 | 604/22 |
| 6,170,358 B1 * | 1/2001 | Hunter | B23Q 16/10 | 33/1 PT |
| 7,886,637 B2 * | 2/2011 | Campbell | B25B 13/105 | 29/700 |
| 7,909,873 B2 * | 3/2011 | Tan-Malecki | A61B 17/1617 | 606/86 R |
| 8,500,173 B2 * | 8/2013 | Zahler | A61B 1/00105 | 285/308 |
| 2004/0147909 A1 * | 7/2004 | Johnston | A61B 17/32002 | 606/1 |
| 2005/0273084 A1 * | 12/2005 | Hinman | A61B 1/008 | 606/1 |
| 2006/0089628 A1 * | 4/2006 | Whitman | A61B 17/1626 | 606/1 |
| 2006/0195070 A1 * | 8/2006 | Hagn | A61B 19/22 | 606/1 |
| 2006/0287642 A1 * | 12/2006 | Perlin | A61B 17/29 | 606/1 |
| 2006/0287643 A1 * | 12/2006 | Perlin | A61B 17/29 | 606/1 |
| 2007/0055219 A1 * | 3/2007 | Whitman | A61B 17/00234 | 606/1 |
| 2007/0203477 A1 * | 8/2007 | Lechot | A61B 17/1666 | 606/1 |
| 2007/0233053 A1 * | 10/2007 | Shelton, IV | A61B 17/07207 | 606/1 |
| 2008/0294192 A1 * | 11/2008 | Stefan | A61B 17/1608 | 606/205 |
| 2011/0166575 A1 * | 7/2011 | Assell | A61B 17/1617 | 606/79 |
| 2011/0295242 A1 * | 12/2011 | Spivey | A61B 19/2203 | 606/1 |

FOREIGN PATENT DOCUMENTS

| | | |
|---|---|---|
| EP | 2316358 A1 | 5/2011 |
| EP | 2489315 A1 | 8/2012 |

* cited by examiner

MEDICAL INSTRUMENT

FIELD OF THE INVENTION

The invention relates to a medical instrument with a shaft, at the proximal end of which a handle is arranged, wherein the shaft is mounted so as to be rotatable about its longitudinal axis with respect to the handle, or a distal shaft main part is rotatable with respect to a proximal part of the shaft acting as a connection element, and can be secured in various positions of rotation relative to the handle via a locking mechanism.

BACKGROUND OF THE INVENTION

Medical instruments with a shaft that is rotatable about its longitudinal axis are known in practice in particular in instruments having an at least partially curved shaft.

In these known instruments, the shaft is fixed by frictional engagement or form-fit engagement. The fixing arrangements by form-fit engagement, where shaped parts corresponding to one another engage in one another, generally have only a small number of adjustment steps.

Although the fixing of the shaft by frictional engagement has the advantage that the shaft can be rotated steplessly, this type of fixing also has the disadvantages that, on the one hand, a relatively high force has to be applied in order to clamp the component parts firmly against each other and, on the other hand, the fixing by frictional engagement is very susceptible to wear and, in addition, can have functional problems in the presence of moisture.

Proceeding from this, the problem addressed by the invention is that of designing a medical instrument with a shaft rotatable about its axis in such a way that this instrument, while being easy to handle, permits a large number of secure and positionally precise rotations of the shaft with respect to the handle, but at the same time takes up the least possible space.

SUMMARY OF THE INVENTION

According to the invention, the solution to this problem is characterized in that the locking mechanism is designed as a latching mechanism which has at least one perforated disk, provided with recesses, and also latching elements, wherein the latching elements and/or the at least one perforated disk are spring-loaded relative to each other, and at least one latching element engages in a corresponding recess of the at least one perforated disk in order to fix the shaft. As an alternative to the perforated disk, it is also possible to use a plate with a contour, e.g. recesses extending in a radiating pattern or radially. In this case, at least one latching element would again engage in a corresponding recess or a setback in the contour of the perforated disk, in order to fix the shaft.

The design of the locking mechanism as a latching mechanism, with spring-loaded latching elements that engage in recesses of a perforated disk, represents a simple and reliable way of adjusting and fixing the rotation of the shaft, permitting a large number of positionally precise fixing steps.

In order to increase the number of latching steps using the same perforated disk, it is proposed, in a preferred embodiment of the invention, that the latching elements are spring-loaded in the direction of the at least one perforated disk, and that the distance between two latching elements arranged next to each other differs from the distance between two recesses arranged next to each other on the at least one perforated disk. In a design where the distance between two latching elements arranged next to each other is half the distance between two recesses arranged next to each other on the perforated disk, the number of the fixing steps achievable with this perforated disk doubles. In this embodiment, only half of the latching elements engage in the recesses at one time.

According to a practical embodiment of the invention, it is proposed that, in the position of the locking mechanism in which it fixes the shaft, a latching element pair consisting of two latching elements always engages in two corresponding recesses of the at least one perforated disk, in order to ensure stable and torsionally rigid fixing. Advantageously, the locking mechanism has a plurality of latching element pairs arranged next to each other, in order to permit a plurality of fixing steps.

Also with the locking by means of the latching element pairs engaging in pairs in the recesses of the perforated disk, it is proposed according to the invention that the distance between two latching element pairs arranged next to each other differs from the distance between two recesses arranged next to each other on the at least one perforated disk, such that, according to the unequal distances between the latching element pairs on the one hand and between the recesses of the perforated disk on the other hand, it is possible to greatly increase the number of possible fixing steps with the same perforated disk.

In order to make the diameter of the medical instruments as small as possible even in the area of the locking mechanism, it is proposed according to the invention that the recesses in the at least one perforated disk are designed extending in the axial direction of the shaft, and the latching elements are arranged axially with respect to the longitudinal axis of the shaft.

For the arrangement of the latching elements, it is proposed in a practical embodiment of the invention that the latching elements are mounted in at least one latching disk arranged parallel to the at least one perforated disk.

According to an alternative embodiment of the invention, it is further proposed that a latching disk provided with latching elements is in each case arranged upstream and downstream of the at least one perforated disk as seen in the axial direction of the shaft.

It is further proposed according to the invention that the latching elements or the at least one perforated disk are movable relative to each other in a direction away from each other in order to release the locking mechanism. According to the invention, the locking is advantageously canceled by the fact that the at least one latching disk is movable away from the at least one perforated disk in the axial direction of the shaft.

To ensure that the shaft in the unlocked position can be rotated as easily as possible to a new position, it is proposed according to an advantageous embodiment of the invention that the at least one latching disk, at least in the position releasing the locking mechanism, can be fixed against the axial mobility via a catch device.

For manual actuation of the locking mechanism, it is proposed by the invention that the at least one perforated disk is rotatable about the longitudinal axis of the shaft via an adjustment device.

To make the handling of the locking mechanism according to the invention particularly simple, it is further proposed that the at least one latching disk is also movable in the axial direction of the shaft via the adjustment device.

Finally, in an alternative embodiment of the invention, it is proposed that the recesses in the perforated disk are designed extending in the radial direction of the perforated disk, and the latching elements are arranged radially in a star shape around the perforated disk. This design has a greater diameter in the radial direction than the axial orientation of the latching elements, but this arrangement of the latching elements permits a shorter design in the axial direction.

It is further proposed by the invention that the shaft can be secured releasably on the handle via a coupling mechanism, as a result of which it is possible for the shaft designed according to the invention to be secured on different handles depending on the intended use.

BRIEF DESCRIPTION OF THE DRAWINGS

Further features and advantages of the invention will become clear from the attached drawings, in which various illustrative embodiments of a medical instrument according to the invention are depicted purely by way of example, without limiting the invention to these illustrative embodiments. In the drawings:

FIG. 6b shows a schematic front view of the latching disks of the locking mechanism according to FIG. 6a.

DETAILED DESCRIPTION OF THE INVENTION

Figure 1:
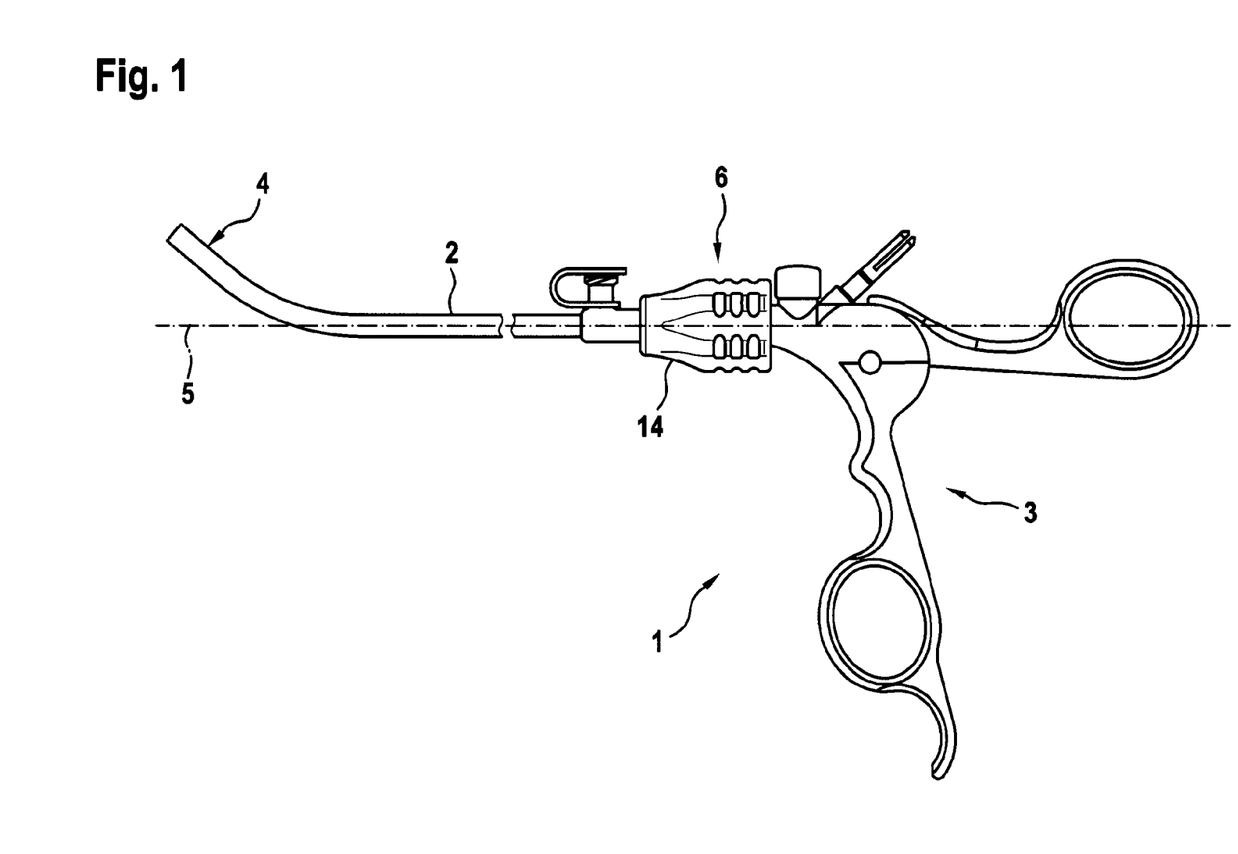
FIG. 1 shows a side view of a medical instrument according to the invention.
Figure 2:
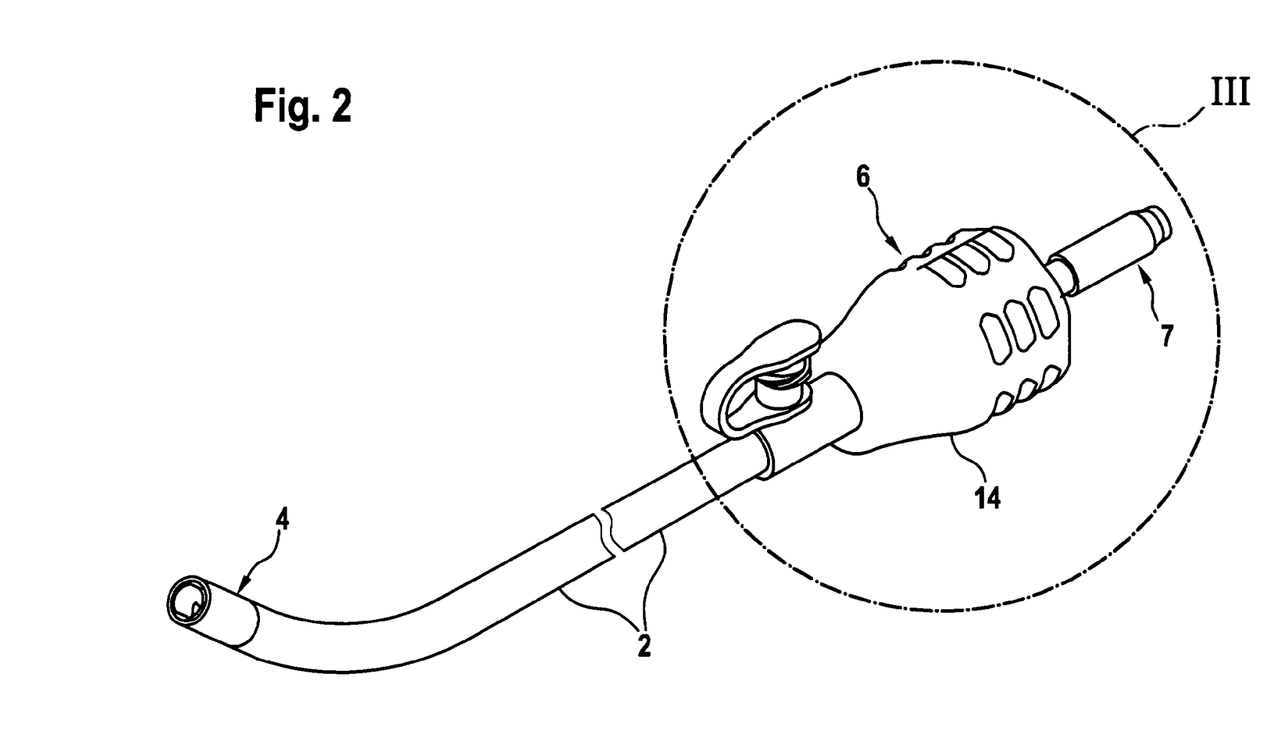
FIG. 2 shows a perspective view of the shaft released from the medical instrument.
Figure 3A:
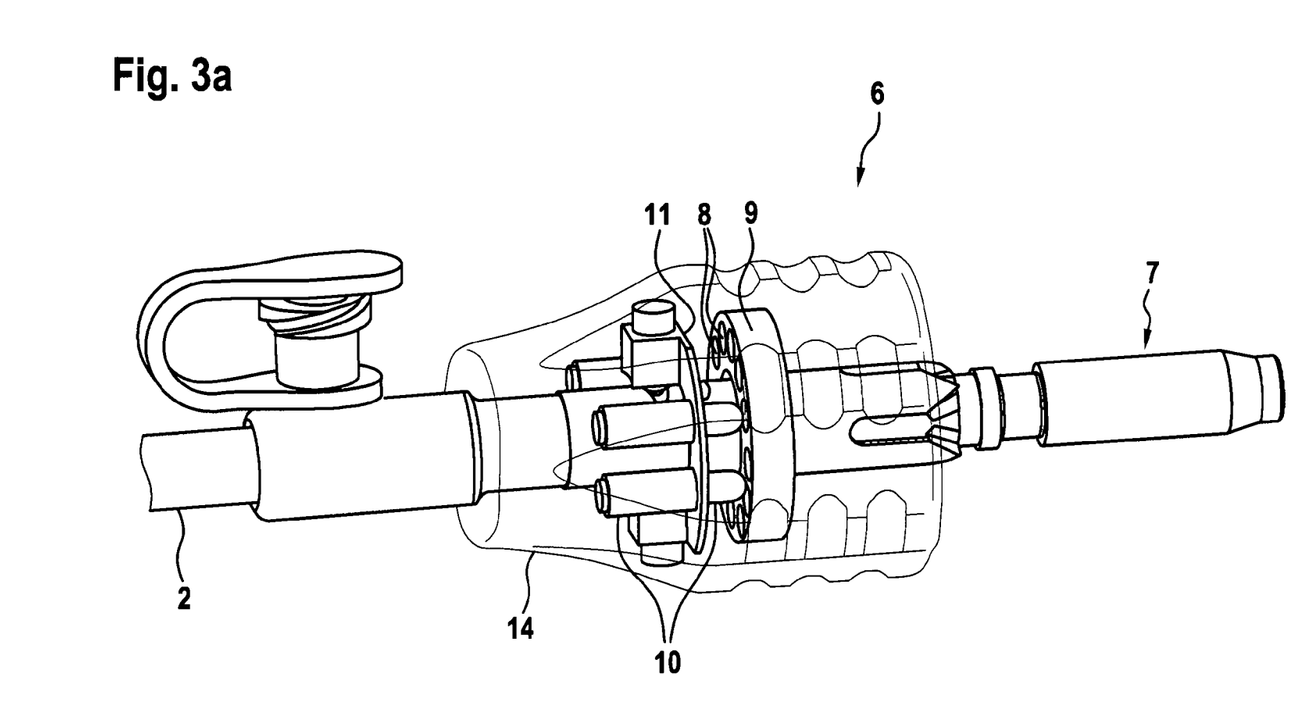
FIG. 3a shows an enlarged view of the detail III according to FIG. 2 in a partially transparent perspective view in an unlocked position.
Figure 3B:
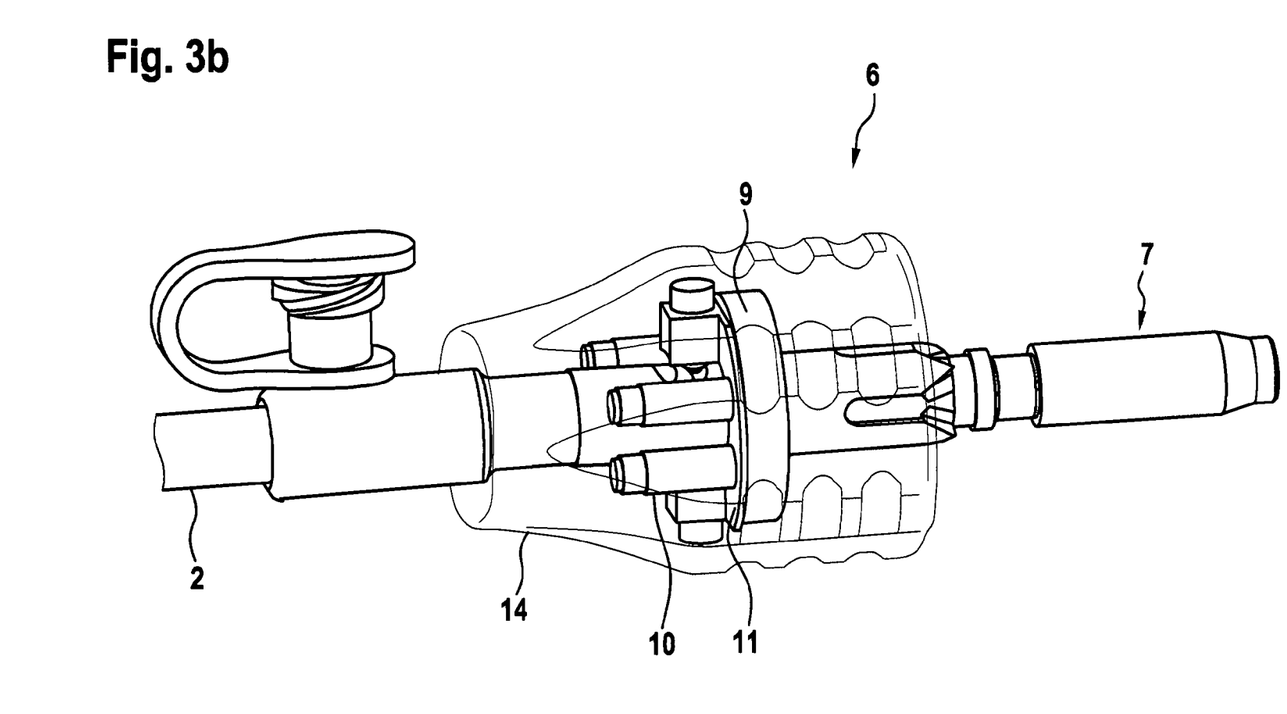
FIG. 3b shows an enlarged view of the detail III according to FIG. 2 in a partially transparent perspective view in a locked position.

The illustration in FIG. 1 shows a side view of a medical instrument 1 with a shaft 2, at the proximal end of which a handle 3 is arranged. As will also be seen from FIG. 1, the shaft 2, in the area of its distal end 4, is angled with respect to the longitudinal axis 5 of the shaft 2. Other configurations of the shaft are of course also possible.

To permit precise positioning of the distal end 4 (angled according to this embodiment) of the shaft 2 and therefore also of a medical tool (not shown) arranged in the hollow shaft 2, the shaft 2 is mounted on the handle 3 so as to be rotatable about its longitudinal axis 5 and can be secured in various positions of rotation relative to the handle 3 via a locking mechanism 6.

In the embodiments shown in the illustrations in FIG. 2 to FIG. 7, the shaft 2 can be secured releasably on the handle via a coupling mechanism 7 arranged proximally on the shaft 2, wherein the locking mechanism 6 is arranged at the proximal end of the shaft 2.

Alternatively, it is of course also possible to arrange the locking mechanism 6 directly on the handle 3.

In the embodiments shown, the locking mechanism 6 is designed as a latching mechanism, which has at least one perforated disk 9, provided with recesses 8, and also latching elements 10, wherein the latching elements 10 and/or the at least one perforated disk 9 are spring-loaded relative to each other, and at least one latching element 10 engages in a corresponding recess 8 of the at least one perforated disk 9 in order to fix the shaft 2.

In the embodiments shown, in order to ensure a stable and torsionally rigid fixing of the shaft 2 in the position of the locking mechanism 6 in which it fixes the shaft 2, a latching element pair 10 consisting of two latching elements 10 always engages in two corresponding recesses 8 of the at least one perforated disk 9.

In the embodiments shown in the illustrations in FIGS. 3a to 6b, the recesses 8 of the at least one perforated disk 9 are designed extending in the axial direction of the shaft 2, and the latching elements 10 are arranged axially with respect to the longitudinal axis 5 of the shaft 2. This configuration allows the diameter of the medical instrument 1 to be kept as small as possible even in the area of the locking mechanism 6, which is advantageous particularly when using the medical instrument 1 for endoscopic purposes.

As will also be seen from the illustrations in FIG. 3a to FIG. 6b, the latching elements 10 in the embodiments shown are mounted and guided in latching disks 11. The latching disks 11 ensure a precise targeting of the latching elements 10 relative to the corresponding recesses 8 of the perforated disk 9.

Figure 6A:
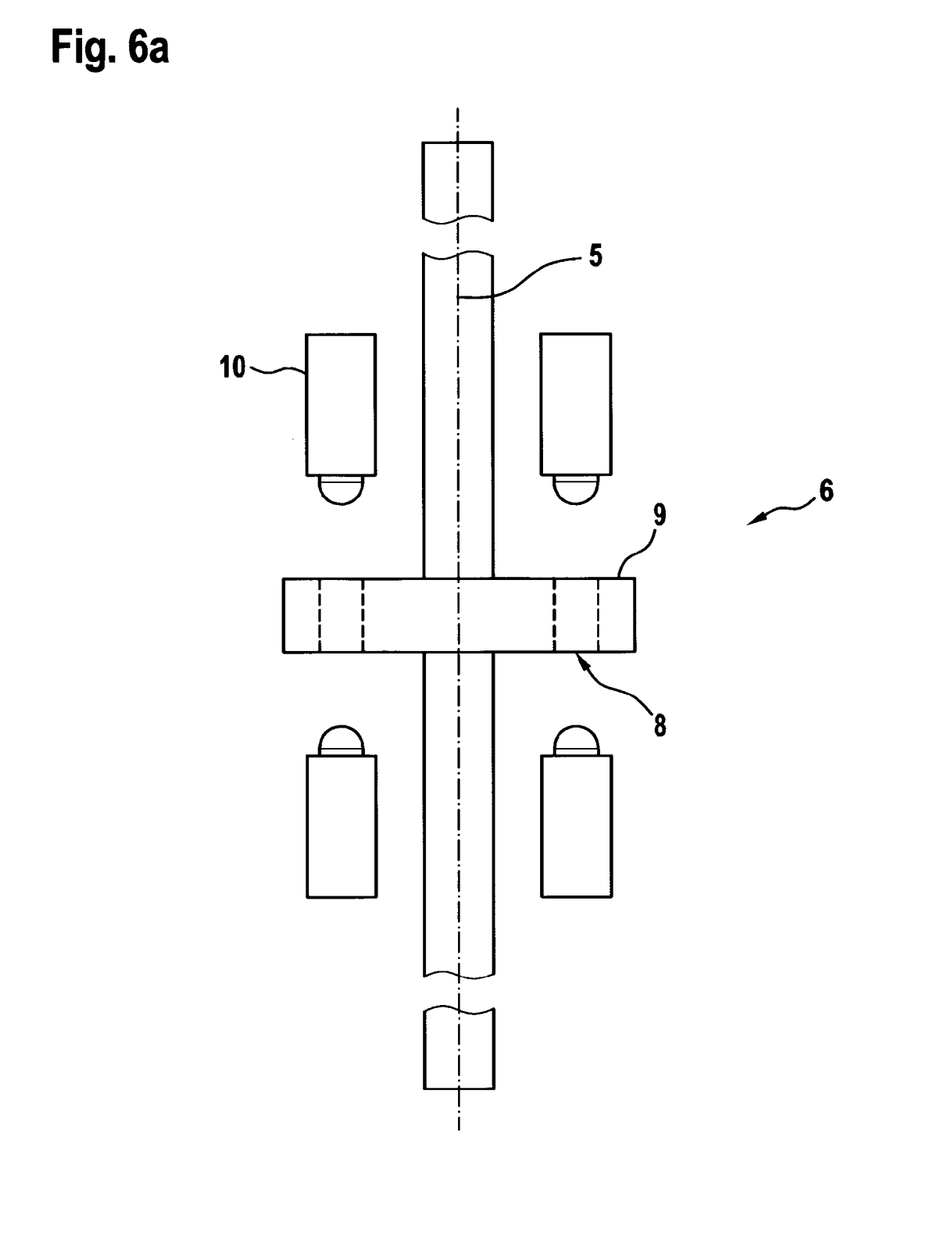
FIG. 6a shows a schematic side view of an alternative embodiment of the locking mechanism.
Figure 6B:
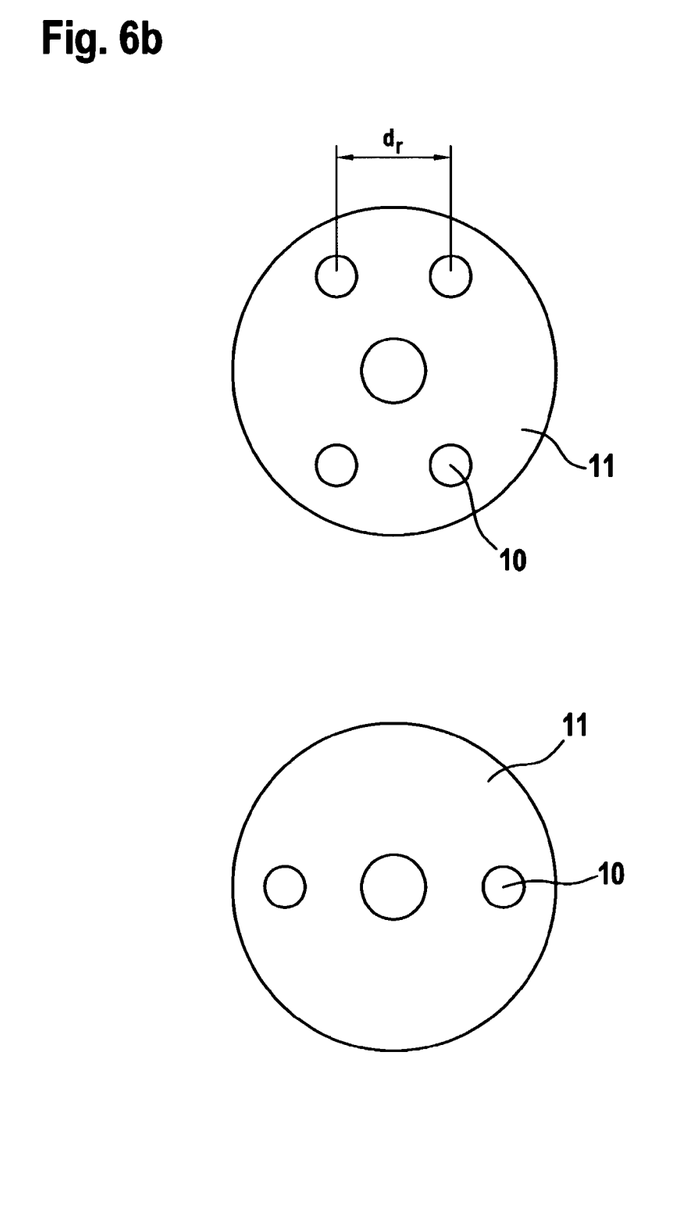
Figure 7:
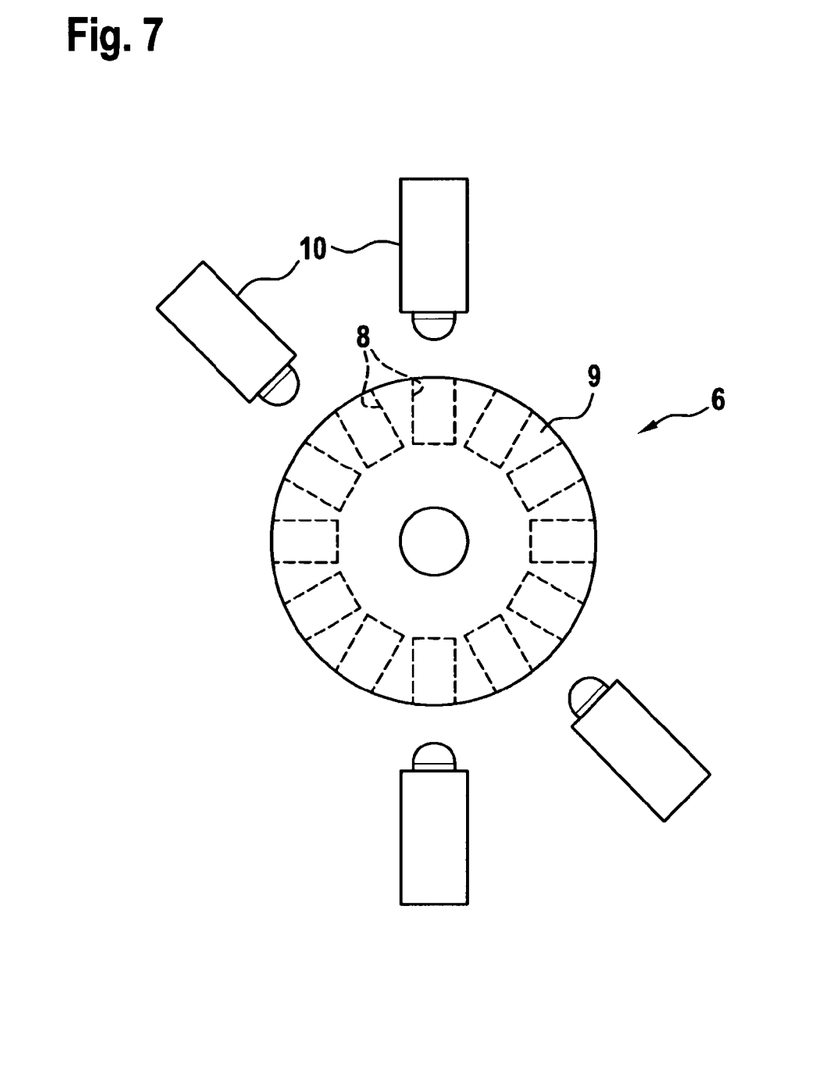
FIG. 7 shows a schematic front view of another alternative embodiment of the locking mechanism.

In the alternative embodiment shown in FIG. 7, the recesses 8 of the perforated disk 9 are designed extending in the radial direction of the perforated disk 9, and the latching elements 10 are arranged radially in a star shape around the perforated disk 9. This design has a greater diameter in the radial direction than the axial orientation of the latching elements 10 according to FIG. 3a to FIG. 6b, but this arrangement of the latching elements 10 permits a shorter design of the medical instrument 1 in the axial direction.

Figure 4:
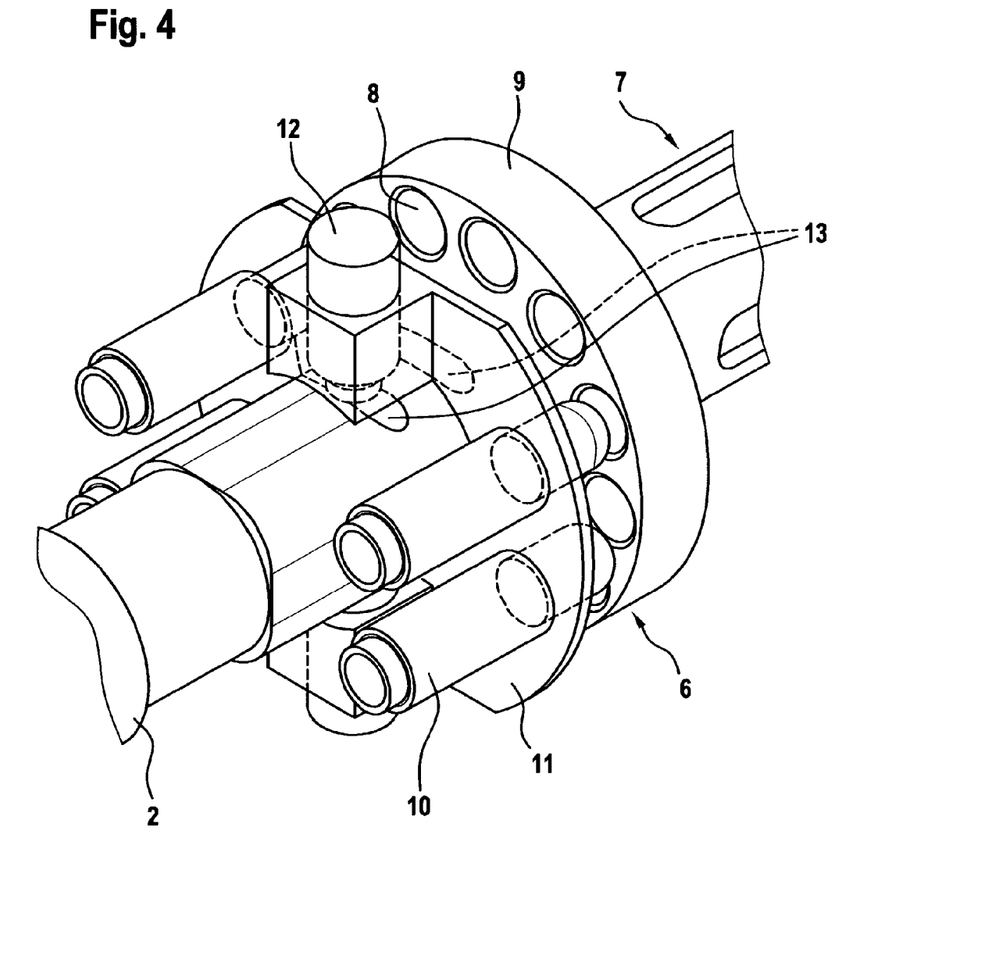
FIG. 4 shows a perspective front view of the locking mechanism according to FIG. 3.
Figure 5:
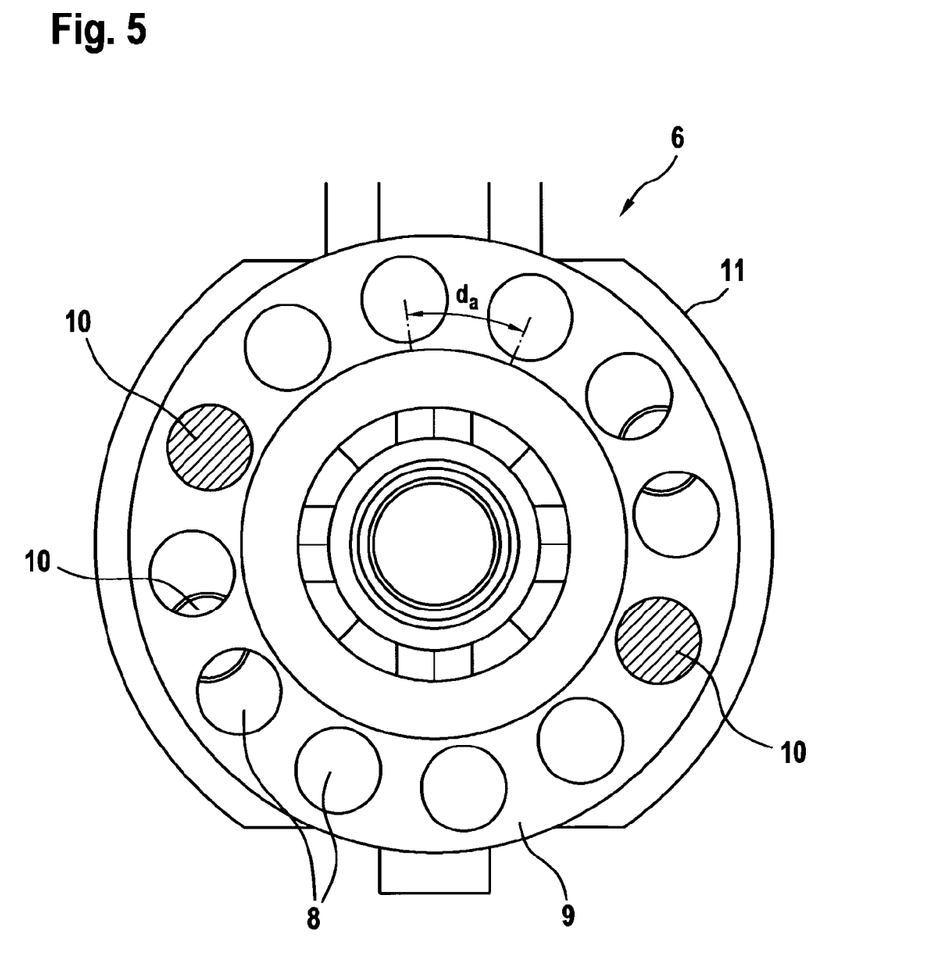
FIG. 5 shows a rear view of the illustration according to FIG. 4.

As will be seen from FIGS. 4 and 5, in the position fixing the shaft 2, a latching element pair 10 in each case engages in corresponding recesses 8 of the perforated disk 9 and thus prevents further rotation of the shaft 2 about the longitudinal axis 5 thereof. All the latching elements 10 are spring-loaded in the direction of the perforated disk 9 via a spring element (not shown), in order to ensure a secure locking of the latching elements 10 with the recesses 8 of the perforated disk 9.

To be able to obtain the greatest possible number of positionally precise fixing steps with one and the same perforated disk 9, the latching elements 10 are arranged such that not all latching elements 10 are simultaneously received in the recesses 8 of the perforated disk 9. As will be seen in particular from FIG. 5, a latching element pair 10 consisting of two latching elements 10 adopts an intermediate position. This adoption of the intermediate position is permitted by the spring-loaded bearing of the latching elements 10, by which latching elements 10 not in engagement with the perforated disk 9 are pushed back.

By virtue of the fact that the distance dr between two latching elements 10 arranged next to each other, as shown in FIG. 6b, differs from the distance $d_a$ between two recesses 8 arranged next to each other on the perforated disk 9, as shown in FIG. 5, it is possible, for example with two latching element pairs, i.e. four individual latching elements, and with twelve recesses 8 in the perforated disk 9, to obtain a total of twenty-four fixing steps.

To release the locking mechanism 6, the latching disk 11 or the perforated disk 9 are arranged on the shaft 2 relative to each other so as to be movable away from each other. As is shown in FIG. 4, the locking is advantageously canceled by the latching disk 11 being movable away from the perforated disk 9 in the axial direction of the shaft 2.

To ensure that the shaft 2 in the unlocked position can be rotated as easily as possible to a new position, the latching disk 11, as can be seen from FIG. 4, can be fixed against axial mobility, at least in the position releasing the locking mechanism 6, via a catch device 12 designed as a ball catch, for example. However, the catch device 12 is advantageously designed such that the latching disk 11 can be fixed axially both in the position releasing the locking mechanism 6 and also in the locking position. For this purpose, the shaft 2 has notches 13, into which the catch device 12 engages in the respective position.

For manual actuation of the locking mechanism 6 according to FIGS. 4 and 5, the perforated disk 9 is rotatable about the longitudinal axis 5 of the shaft 2 via an adjustment device 14, preferably designed as a rotary wheel.

To make the handling of the locking mechanism 6 particularly simple, the adjustment device 14 is preferably designed such that the axial movement of the latching disk 11 can also take place via the adjustment device 14.

The alternative embodiment for the design of the locking mechanism 6, as shown in the illustrations in FIGS. 6a and 6b, differs from the arrangement according to FIGS. 4 and 5 in that, in this second embodiment of the locking mechanism 6, the latching elements 10 are mounted in latching disks 11 which, seen in the axial direction of the shaft 2, are arranged upstream and downstream of the perforated disk 9. In order to increase the number of possible fixing steps, the two latching disks 11, as can be seen from FIG. 6b, have different patterns for the arrangement of the latching elements 10.

As an alternative to the spring loading of the latching elements 10, the locking between the latching elements 10 and the recesses 8 of the perforated disk 9 in the embodiment shown in FIGS. 6a and 6b can also be achieved by the fact that the perforated disk 9 is mounted movably on the shaft 2 in the axial direction and can thus be moved in the direction of both latching disks 11.

A medical instrument 1 constructed in the manner described above is distinguished by the fact that the shaft 2, while being easy to handle, can be rotated more safely and with precise positioning into a large number of fixed positions about its longitudinal axis 5.

The invention claimed is:

1. A medical instrument, comprising:
   a shaft, at a proximal end of which a handle is arranged, the shaft being mounted so as to be rotatable about a longitudinal axis of the shaft with respect to the handle; and
   a locking mechanism adapted to secure the shaft in various positions of rotation relative to the handle;
   wherein the locking mechanism is designed as a latching mechanism which has a perforated disk with recesses, and latching elements;
   wherein each of the latching elements is moveable relative to the perforated disk in a direction parallel to the longitudinal axis of the shaft between
   (i) a latched position in which the latching element engages in a corresponding one of the recesses of the perforated disk in order to prevent rotation of the shaft relative to the handle, and
   (ii) an intermediate position, in which the latching element is not engaged in any one of the recesses of the perforated disk; and
   wherein each of the latching elements includes a spring element that biases the latching element in a direction toward the perforated disk; and
   wherein a distance between two latching elements arranged next to each other differs from a distance between two recesses arranged next to each other on the perforated disk;
   wherein the latching elements include at least a first latching element and a second latching element, and the latching elements are configured such that the first latching element can be in the latched position when the second latching element is in the intermediate position.

2. The medical instrument according to claim 1, wherein, in a position of the locking mechanism which prevents rotation of the shaft relative to the handle, a latching element pair comprises two latching elements engaged in two corresponding recesses of the perforated disk.

3. The medical instrument according to claim 2, wherein the latching elements are arranged circumferentially about the longitudinal axis of the shaft, and are grouped into a plurality of latching element pairs, each including a first latching element and a second latching element arranged next to each other in a first circumferential direction about the longitudinal axis of the shaft.

4. The medical instrument according to claim 3, wherein the recesses are arranged circumferentially about the longitudinal axis of the shaft, and are grouped into a plurality of recess pairs, each including a first recess and a second recess arranged next to each other in a second circumferential direction about the longitudinal axis of the shaft;
   wherein a distance in the first circumferential direction between the first latching element and the second latching element differs from a distance in the second circumferential direction between the first recess and the second recess.

5. The medical instrument according to claim 1, wherein the recesses of the perforated disk extend in a direction parallel to the longitudinal axis of the shaft, and each of the latching elements extends longitudinally in a direction parallel to the longitudinal axis of the shaft.

6. The medical instrument according to claim 5, wherein the latching elements are mounted in a latching disk arranged parallel to the perforated disk.

7. The medical instrument according to claim 6, wherein the latching disk is a first latching disk and is arranged upstream of the perforated disk as seen in a direction of the longitudinal axis of the shaft; and
   wherein the medical instrument further comprises a second latching disk arranged downstream of the perforated disk as seen in the direction of the longitudinal axis of the shaft.

8. The medical instrument according to claim 1, wherein the perforated disk is rotatable about the longitudinal axis of the shaft via an adjustment device.

9. The medical instrument according to claim 8, wherein a latching disk, on which the latching elements are mounted, is movable in a direction parallel to the longitudinal axis of the shaft via the adjustment device.

10. The medical instrument according to claim 8, further comprising a medical tool arranged at least partially in the shaft.

11. The medical instrument according to claim 1, wherein the shaft is releasably secured on the handle via a coupling mechanism.

12. The medical instrument according to claim 1, wherein the latching mechanism includes at least three latching elements, each of the latching elements being arranged at a different circumferential position about the longitudinal axis of the shaft.

13. The medical instrument according to claim 12, wherein the latching mechanism includes at least four latching elements.

14. The medical instrument according to claim 1, wherein the recesses each extend along a respective axis parallel to the longitudinal axis of the shaft, and the latching elements each extend along a respective axis parallel to the longitudinal axis of the shaft.

15. The medical instrument according to claim 1, wherein a distance between two latching elements arranged next to each other in a first circumferential direction about the longitudinal axis of the shaft differs from a distance between two recesses arranged next to each other in a second circumferential direction about the longitudinal axis of the shaft.

* * * * *

UNITED STATES PATENT AND TRADEMARK OFFICE
CERTIFICATE OF CORRECTION

| | | |
|---|---|---|
| PATENT NO. | : 9,445,792 B2 | |
| APPLICATION NO. | : 14/163769 | |
| DATED | : September 20, 2016 | |
| INVENTOR(S) | : Daniel Kärcher | |

It is certified that error appears in the above-identified patent and that said Letters Patent is hereby corrected as shown below:

On the Title Page

Page 1, Column 2, (57) Abstract, Line 4:
"positions of rotation relative to the handle via a licking"

Should read:
--positions of rotation relative to the handle via a locking--

Page 1, Column 2, (57) Abstract, line 9:
"shaft with respect to the handle, the licking mechanism is"

Should read:
--shaft with respect to the handle, the locking mechanism is--

Signed and Sealed this
Twenty-first Day of February, 2017

Michelle K. Lee
*Director of the United States Patent and Trademark Office*